(12) United States Patent
Basset et al.

(10) Patent No.: US 10,179,326 B2
(45) Date of Patent: *Jan. 15, 2019

(54) SUPPORTED IRON CATALYSTS, METHODS OF MAKING, METHODS OF HYDROCARBON DECOMPOSITION

(71) Applicant: King Abdullah University of Science and Technology, Thuwal (SA)

(72) Inventors: Jean-Marie Basset, Thuwal (SA); Lu Zhou, Thuwal (SA); Youssef Saih, Thuwal (SA); Linga Enakonda Reddy, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 7 days.

This patent is subject to a terminal disclaimer.

(21) Appl. No.: 14/955,609

(22) Filed: Dec. 1, 2015

(65) Prior Publication Data

US 2016/0129423 A1  May 12, 2016

Related U.S. Application Data

(63) Continuation-in-part of application No. 13/746,936, filed on Jan. 22, 2013.

(Continued)

(51) Int. Cl.
*B01J 23/745* (2006.01)
*B01J 37/00* (2006.01)
(Continued)

(52) U.S. Cl.
CPC ......... *B01J 23/745* (2013.01); *B01J 37/0036* (2013.01); *B01J 37/08* (2013.01); *C01B 3/26* (2013.01); *C07C 2/76* (2013.01); *C01B 2203/0277* (2013.01); *C01B 2203/107* (2013.01); *C01B 2203/1047* (2013.01); *C01B 2203/1052* (2013.01);
(Continued)

(58) Field of Classification Search
CPC ....................................................... B01J 23/745
See application file for complete search history.

(56) References Cited

U.S. PATENT DOCUMENTS

| 7,473,814 B2 | 1/2009 | Basset et al. |
| 7,858,068 B2 | 12/2010 | Fuller et al. |

(Continued)

FOREIGN PATENT DOCUMENTS

| CN | 1659120 A | 8/2005 |
| CN | 101300191 A | 11/2008 |

(Continued)

OTHER PUBLICATIONS

Balakrishnan et al, "Hydrogen production from methane in the presence of red mud-making mud magnetic," Green Chem., 2009, 11, pp. 42-47 (Year: 2008).*

(Continued)

*Primary Examiner* — Colin W. Slifka
(74) *Attorney, Agent, or Firm* — Billion & Armitage; Benjamin C. Armitage

(57) ABSTRACT

Embodiments of the present disclosure also provide for a supported fused Fe catalyst, a method of making the supported fused Fe catalyst, methods of hydrocarbon decomposition, and the like.

4 Claims, 7 Drawing Sheets

Related U.S. Application Data

(60) Provisional application No. 61/589,689, filed on Jan. 23, 2012.

(51) Int. Cl.
| | |
|---|---|
| *B01J 37/08* | (2006.01) |
| *C01B 3/26* | (2006.01) |
| *C07C 2/84* | (2006.01) |
| *C07C 2/76* | (2006.01) |

(52) U.S. Cl.
CPC ............... *C01B 2203/1064* (2013.01); *C01B 2203/1082* (2013.01); *C07C 2521/04* (2013.01); *C07C 2523/46* (2013.01); *C07C 2523/745* (2013.01); *C07C 2523/75* (2013.01)

(56) References Cited

U.S. PATENT DOCUMENTS

| | | | |
|---|---|---|---|
| 2004/0122115 A1* | 6/2004 | Espinoza | B01J 23/8946 518/721 |
| 2004/0220437 A1* | 11/2004 | Jothimurugesan | B01J 23/745 585/300 |
| 2005/0272966 A1* | 12/2005 | Basset | C07C 2/76 585/708 |
| 2008/0263954 A1* | 10/2008 | Hammel | B01J 23/882 48/127.9 |
| 2010/0068571 A1* | 3/2010 | Collings | C01B 3/323 429/411 |
| 2010/0280176 A1 | 11/2010 | Biswas et al. | |
| 2011/0053020 A1* | 3/2011 | Norton | B01J 21/063 429/425 |
| 2011/0294908 A1* | 12/2011 | Wu | B01J 23/78 518/713 |
| 2012/0219490 A1 | 8/2012 | Noda et al. | |
| 2014/0328749 A1 | 11/2014 | Hammel et al. | |

FOREIGN PATENT DOCUMENTS

| | | |
|---|---|---|
| DE | 3116409 A1 | 11/1982 |
| GB | 363735 A | 12/1931 |
| GB | 2253858 A | 9/1992 |
| JP | 2007090342 A | 4/2007 |
| RU | 2312059 C1 | 12/2007 |
| WO | 03104171 A1 | 12/2003 |
| WO | 2006040788 | 4/2006 |
| WO | 2009115805 A1 | 9/2009 |
| WO | 2011107822 | 9/2011 |

OTHER PUBLICATIONS

Paredes et al, "Catalytic combustion of methane over red mud-based catalysts," Applied Catalysis B: Environmental 47 (2004), pp. 37-45 (Year: 2004).*

"International Search Report and Written Opinion", International Application No. PCT/IB2013/000472, dated Jul. 11, 2013, 10 pages.

Amariglio, et al., J. Catal. 177, 113, 1998.

Amariglio, et al., "Carbon monoxide induced desorption of alkanes and alkenes up to C8 after chemisorption of methane on platinum", Catalysis LEtters, 31, 1995, 19-26.

Amariglio, et al., "Periodic operation of a catalyst as a means of overcoming a thermodynamic constraint. The case of methane homologation on metals", Catalysis Today, 25,, 1995, 113-125.

Amenomiya, et al., "Conversion of Methane by Oxidative Coupling", Catal.Rve.Sci.Eng., 32, 1963, 1990.

Ashok, et al., "Catalytic Decomposition of Methane to Hydrogen and Carbon Nanofiberes over Ni—Cu—SiO2 Catalysts", Energy & Fuels, 23, 2009, 5-13.

Beckerle, et al., "Collision induced dissaciative chemisorption of CH4 on NI(111) by inert gas atoms: The mechanism for chemistry with a hammer", J. Chem. Phys. 91,, 1989, 5756-5777.

Belgued, et al., "Oxygen-Free Conoversion of Methane to Higher Alkanes through an Isothermal Two Step reaction on Ruthenium", Journal of Catalysis 161, 1996, 282-291.

Belgued, et al., "Oxygen-Free Conversion of Methane to Higher Alkanes through an Isothermal Two-Step Reaction on Platinum (EUROPT-1)", Journal of Catalysis, 159, 1996, 441-448.

Bradford, "Isotherma, non-oxidative, two-step CH4 conversion over unsupported and supported Ru and Pt catalysts", Catal. 66,, 2000, 113-120.

Carstens, et al., "Methane Activation and Conversion to Higher Hydrocarbons on Supported Ruthenium", J. Catal. 161, Aarticle No. 0200, 1996, 423-429.

Choudhary, et al., "Hydrogen Production via Catalytic Decomposition of Methane", Journal of Catalysis, 199,, 2001, 9-18.

Duncan, et al., "The Characterization of Alkyl Intermediates on Silica-Supported Ruthenium with 13C Nuclear Magnetic Resonance Spectroscopy", Journal of Catalysis 95,, 1985, 305-308.

Duncan, et al., "The Characterization of Carbonaceous Species on Ruthenium Catalysts with 13C Nuclear Magnetic resonance Spectroscopy", Journal of Catalysis, 93,, 1985, 1-22.

Dunker, et al., "Production of hydrogen by thermal decomposition of methane in a fluidized-bed reactor-Effects of catalyst, temperature, and residence time", Int J. Hydrogen Energy, 31, 2006, 473-484.

Ermakova, et al., "Effective catalysts for direct cracking of methane to produce hydrogen and filamentous carbon Part I. Nickel catalysts", Appl Catal A, 201, 2000, 61-70.

Guczi, et al., ""One-Step" Methane Conversion under Non Oxidative Condition over Pt—Co/NaY Catalysts at low Temperature", Stud. Surf. Sci. Catal., 119,, 1998, 295-300.

Guczi, et al., "Comparative study on hydrogen-assisted "one-step" methane conversion over Pd—Co/SiO2 and Pt—Co/NaY catalysts", Catal. Today, 64,, 2001, 91-96.

Guczi, et al., "Low-Temperature Methane Activation under Nonoxidative Conditions over Supported Ruthenium-Cobalt Bimetallic Catalysts", J. Catal., 167,, 1997, 495-502.

Guczi, et al., "Non-oxidative methane coupling over Co—Pt/NaY bimetallic catalysts", Catal. Lett. 39,, 1996, 43-47.

Holmen, et al., "Pyrolysis of natural gas: chemistry and process concepts", Fuel Process. Technology, 42, 1995, 249-267.

Jang, et al., "Hydrogen production by the thermocatalytic decomposition of methane in a fluidized bed reactor", Korean J. Chem. Eng., 24(2), 2007, 374-377.

Johnson, et al., "Hydrogen Embedded in Ni: Production by Incident Atomic Hydrogen and Detection by High-Rresolution Electron Energy Loss", Physical Review Letters, vol. 67, No. 7, 1991, 927-930.

Jung, et al., "Hydrogen production by catalytic decomposition of methane over carbon catalysts in a fluidized bed", Korean J. Chem. Eng., 24(4), 2007, 674-678.

Kassel, "The Thermal Decomposition of Methane", Contribution from the Pittsburgh Experiment Station of the U.S. Bureau of Mines, Oct. 5, 1932, 3949-3961.

Kim, et al., "Hydrogen production by catalytic decomposition of Methane over activated carbons: kinetic study", Int J. Hydrogen Energy, 29, 2004, 187-193.

Koerts, et al., "A Low temperature Reaction Sequence for Methane Conversion", J.Chem. Soc., Chem, Commun.,, 1991, 1281-1283.

Koerts, et al., "Homologation of Olefins with Methane on Transition Metals", J. Am. Chem. Soc. 114,, 1992, 7272-7278.

Koerts, et al., "Hydrocarbon Formation from Methane by a Low-Temperature Two-Step Reaction Sequence", Journal of Catalysis 138,, 1992, 101-114.

Koerts, et al., "Mechanism of carbon-carbon bond formation by transition metals", J. Mol. Catal. 74, 185, 1992, 185-191.

Koerts, et al., "The reaction path for recombination of surface CHx species", Journal of Molecular Catalysis, 70,, 1991, 119-127.

Lee, et al., "Dynamics of the activated dissociative chemisorption of CH4 and implication for the pressure gap in catalysis: A molecular beam-high resolution electron energy loss study", The Journal of Chemical Physics, 87,, 1987, 2724-2741.

(56) References Cited

OTHER PUBLICATIONS

Li, et al., "Simultaneous Production of Hydrogen and Nanocarbon from Decomposition of Methane on a Nickel-Based Catalyst", Energy & Fuels, 14, 2000, 1188-1194.
Marceau, et al., "Influence of the Hydrogenation Step on Selectivity during the Nonoxidative Oligomerization of Methane to Alkanes on Pt/SiO2 Catalysts (EUROPt-1)", J. Catal., 183,, 1999, 384-395.
Moliner, et al., "Thermocatalytic decomposition of methan over activated carbons: influence of textural properties and surface chemistry", Int J Hydrogen Energy, 30, 2005, 293-300.
Muradov, et al., "Catalytic activity of carbons for methane decomposition reaction", Catal. Today 102-103, 2005, 225-233.
Muradov, "CO2-Free Production of Hydrogen by Catalytic Pyrolysis of Hydrobarcon Fuel", Energy and Fuels, 12(1), 1998, 41-48.
Muradov, "How to Produce Hydrogen from Fossil Fuels Without CO2 Emission", Int. J. Hydrogen Energy, vol. 18, No. 3, 1993, 211-215.
Murata, et al., "Improvement of Stability of an Fe?Mg/Al2O3 Catalyst for the Decomposition of Methane in the Presence of O2/CO2", React Kinet. Catal. Lett. , vol. 80(1), 2003, 39-44.
Olah, "Electrophilic Methane Conversion", Acc. Chem.Res., 20,, 1987, 422-428.
Olsvik, et al., "Thermal Coupling of methane. A comparison between kinetic model data and experimental data", Thermochimica Acta, 232, 1994, 155-169.
Otsuka, et al., "Decomposition of methane over Ni catalysts supported on carbon fibers formed from different dydrocarbons", Carbon, 41, 2003, 223-233.
Otsuka, et al., "Production of pure hydrogen by cyclic decomposition of methane and oxidative elminiation of carbon nanofibers on supported-Ni-based catalysts", Appl Catal A, 273, 2004, 113-124.
Pareja, et al., "Increasing the yield in Methane homologation through an isothermal two-reaction sequence at 250 degreesC onn platinum", Catalysis Today, 21, 226, 1994, 423-430.
Poirier, et al., "Catalytic Decomposition of Natural Gas to Hydrogen for Fuel Cell Applications", Int. J. Hydrogen Energy, vol. 22, No. 4, 1997, 429-433.
Polshettiwar, et al., "High-Surface-Area Silica Nanospheres (KCC-1) with a Fibrous Morphology", Angew. Chem. Int Ed. 2010, 49, 1-6.
Reshetenko, et al., "Coprecipitated iron-containing catalysts (Fe—AlsO3, Fe—Co—Al2O3, Fe—Ni—Al2O3) for methane decomposition at moderate temperatures PartII. Evolution of the catalysts in reaction", Appl Catal A, 270, 2004, 87-99.
Sault, et al., "Model Studies of Surface Catalyzed Reactions", Advances in Chemical Physics, 76,, 1989, 153-210.
Shah, et al., "Hydrogen Production by Catalytic Decomposition of Methane", Energy and Fuels, 15, 2001, 1528-1534.
Sherry, et al., J.American Chem. Soc.,112, 1987, 1259-1261.
Solymosi, et al., "Decomposition of CH4 over Supported Pd Catalysts", J. Catal., 147,, 1994, 272-278.
Solymosi, et al., "Enhanced formation of ethane in the conversion of methane over Cu—Rh/SiO2", Catal. Lett., 34,, 1995, 343-350.
Steinberg, "The Hy-C Process (Thermal Decomposition of Natural Gas) Potentially the Lowest Cost Source of Hydrogen with the Least CO2 Emission", Energy Convers. Mgmt. vol. 36(6-9), 1995, 791-796.
Suelves, et al., "Hydrogen production by thermo catalytic decomposition of methane on Ni-based catalysts: influence of operating conditions on catalyst deactivation and carbon characteristcs", Int. J. Hydrogen Energy, 30, 2005, 1555-1567.
Sun, et al., "Kinetics of dissociative chemisorption of methande and ethane on Pt(110)-(1×2)", J.Vac. Sci. Technol. A 8,, 1990, 2445.
Takenaka, et al., "Formation of Carbon Nanofibers and Carbon Nanotubes through Methane Decomposition over Supported Cobalt Catalysts", J. Phys. Chem. B, 108, 2004, 11464-11472.
Takenaka, et al., "Methane Decomposition into Hydrogen and Carbon Nanothers over Supported Pd—Ni Catalysts: characterization of the Catalysts during the Reaction", J. Phys Chem B, 108, 2004, 7656-7664.
Wang, et al., "Formation of filamentous carbon during methane decomposition over Co—MgO Catalysts", Carbon, 40, 2002, 1911-1917.
Winslow, et al., "Application of Transient Response Techniques for Quantitative Determination of Adsorbed Carbon Monoxide and Carbon Present on the Surface of a Ruthenium Catalyst during Fischer-Tropsch Synthesis", Journal of Catalysis 86,, 1984, 158-172.
Wu, et al., "Investigations of Graphitic Overlayers formed from Methane Decomposition on Ru(0001) and Ru(1120) catalysts with scanning tunneling Microscopy and High-Resolution Electron Energy Loss spectroscopy", J. Phys. Chem, 98,, 1994, 5104-5110.
Zein, et al. "Kinetic Studies on Catalytic Decomposition of Methane to Hydrogen and Carbon over Ni/TiO2 Catalysts", Ind. Eng. Chem. Res., 43, 2004, 4864-4870.

* cited by examiner

SUPPORTED IRON CATALYSTS, METHODS OF MAKING, METHODS OF HYDROCARBON DECOMPOSITION

CROSS-REFERENCE TO RELATED APPLICATIONS

This application is a Continuation-In-Part Patent Application of and claims the benefit of and priority to U.S. Utility patent application having Ser. No. 13/746,936, having the title "A process for the decomposition of methane can be controlled to form ethane or hydrogen with a solid carbon product," filed on Jan. 22, 2013, which claims priority to U.S. Patent Application No. 61/589,689, filed Jan. 23, 2012, both of which are hereby incorporated by reference in its entirety.

BACKGROUND

Methane catalytic decomposition (hereinafter MCD) has been widely studied as an alternative way of methane steam reforming (MSR) to produce hydrogen, because MCD reaction does not produce CO or $CO_2$ as by-products, the need for water-gas shift and $CO_2$-removal stages, as required in conventional MSR, is eliminated. Further, except the pure hydrogen produced from this process, the co-produced carbon nanomaterials (CNMs) have also been investigated extensively because of their excellent properties and great potentials for many utilization purposes.

However, because of the catalysts deactivation issue, this process is still far away from the industrialization. Since the main products of MCD are solid carbon and hydrogen gas, the formed carbon will definitely cover the active metal surface and/or block the support pore, thus finally deactivate the catalyst. Some have regenerated the catalysts by burning off the deposited carbon. However, this kind of regeneration of deactivated catalysts will lead to $CO_2$ production and also may result in contamination of hydrogen. Therefore, the design of a stable MCD catalyst is the priority for this process.

SUMMARY

Embodiments of the present disclosure also provide for a supported fused Fe catalyst, a method of making the supported fused Fe catalyst, methods of hydrocarbon decomposition, and the like.

An embodiment of the present disclosure provides for a composition, among others, that includes: a supported fused Fe catalyst, wherein the supported fused Fe catalyst is a fused $Fe/Al_2O_3$ catalyst.

An embodiment of the present disclosure provides for a method of making the supported fused Fe catalyst, among others, that includes: physically grinding and mixing a Fe nitrate and a support nitrate; calcining under static air from about room temperature to 350° C. for about 2 to 4 h with a 3 to 8° C./min latter; reducing the temperature down to room temperature under air flow; and grinding the final sample to fine powder to form the supported fused Fe catalyst.

An embodiment of the present disclosure provides for a method of selectively producing hydrogen or ethane from methane, among others, that includes: selecting a temperature suitable for a metal catalyst and a feed gas including methane to produce a product having a controlled hydrogen/ethane ratio, predominately hydrogen and a solid carbon product or predominately ethane and hydrogen; contacting the feed gas with the metal catalyst at the selected temperature to produce the product, wherein the metal catalyst is a supported fused Fe catalyst, wherein the supported fused Fe catalyst is a fused $Fe/Al_2O_3$ catalyst.

An embodiment of the present disclosure provides for a method for hydrocarbon catalytic decomposition, among others, that includes: heating a supported fused Fe catalyst to about 750° C. under an inert gas; flowing a hydrocarbon across the supported fused Fe catalyst; and decomposing the hydrocarbon to produce $H_2$. In an embodiment, the method can also include: heating the supported fused Fe catalyst to the reduction temperature of the supported fused Fe catalyst; and flowing $H_2$ over the supported fused Fe catalyst to reduce the supported fused Fe catalyst.

BRIEF DESCRIPTION OF THE DRAWINGS

Many aspects of the present disclosure can be better understood with reference to the following drawings.

DETAILED DESCRIPTION

Figure 1:
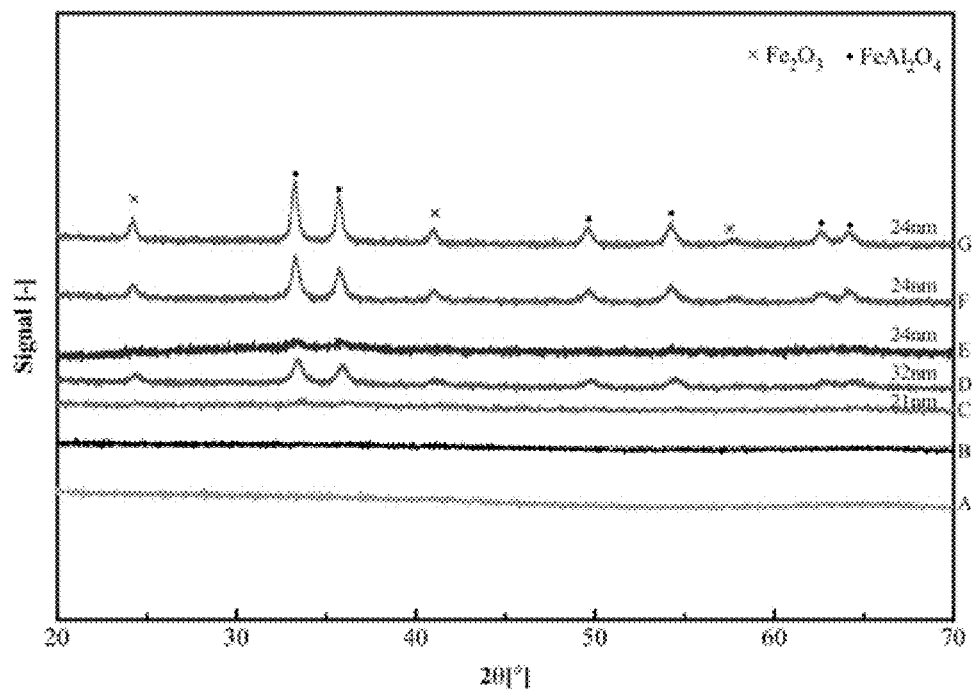
FIG. 1 illustrates XRD results over prepared fresh $Fe/Al_2O_3$ catalysts with fusion method: A: 5 wt % $Fe/Al_2O_3$; B: 10 wt % $Fe/Al_2O_3$; C: 20 wt % $Fe/Al_2O_3$; D: 35 wt % $Fe/Al_2O_3$; E: 40 wt % $Fe/Al_2O_3$; F: 50 wt % $Fe/Al_2O_3$; G: 65 wt % $Fe/Al_2O_3$.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

General Discussion

A.

Methane, which is the main constituent of natural gas, is one of the most widespread sources of hydrogen and carbon in the world. At times, it can be useful to couple methane into ethane in order to use the gas for other purposes. At other times, it can be useful to decompose methane directly into hydrogen and carbon. Advantageously, development of an efficient catalyst that can decompose methane into both hydrogen and solid carbon products, such as carbon black or carbon nanotubes, or methane into ethane, in a selective and controllable manner, can improve economy of hydrogen production.

In one aspect, a method of selectively producing hydrogen or ethane from methane includes selecting a temperature suitable for a metal catalyst and a feed gas including methane to produce a product having a controlled hydrogen/ethane ratio, predominately hydrogen and a solid carbon product or predominately ethane and hydrogen and contacting the feed gas with the metal catalyst at the selected temperature to produce the product.

In another aspect, a method of producing hydrogen includes contacting a feed gas including methane with a ruthenium nanoparticle on a silica nanoparticle support at a temperature suitable to produce a product gas including hydrogen.

In another aspect, a method of selectively producing hydrogen or ethane includes selecting a first pressure and a first temperature suitable to produce hydrogen from methane or a second pressure and a second temperature suitable to produce ethane from methane and contacting a feed gas including methane with a metal catalyst at the selected temperature and selected pressure to produce a product gas including hydrogen or ethane.

In certain embodiments, the selected temperature can be a temperature suitable to produce a product having a hydrogen/ethane ratio of at least 3, at least 5, at least 25, at least 250 or at least 600. In certain other embodiments, the selected temperature can be less than 1000° C., less than 800° C., or greater than 300° C. Selecting the temperature can include choosing a first temperature for the metal catalyst and the feed gas to produce a product gas consisting essentially of hydrogen or a second temperature for the metal catalyst and the feed gas to produce a product gas consisting essentially of ethane and hydrogen.

In certain embodiments, metal catalyst can include ruthenium, nickel, iron, copper, cobalt, palladium, platinum, or combinations thereof. The metal catalyst can be supported on a solid support. The solid support can include a silicon oxide, aluminum oxide, titanium oxide, zirconium oxide, magnesium oxide, cerium oxide, zinc oxide, molybdenum oxide, iron oxide, nickel oxide, cobalt oxide or graphite. The metal catalyst can include other catalysts described herein.

In certain embodiments, the method can include separating the hydrogen from the solid carbon product.

The feed gas can include less than 1000 ppm water or less than 1000 ppm oxygen containing compounds. The feed gas can consist essentially of methane and an inert gas.

The method described herein can increase selectivity and efficiency of methane conversion compared to competitive processes of oxidative coupling, thermal coupling, plasma coupling and non-oxidative catalytic coupling, which are not selective and often require a great deal of energy or temperatures in excess of 1000° C. While thermal decomposition of methane results in production of solid carbon products and hydrogen and can reduce or eliminate greenhouse gas emission, this process typically can require temperatures greater than 1300° C. for complete conversion. A system that allows for decomposition of methane to hydrogen and solid carbon products in a selective manner can significantly improve the commercial viability of methane conversion.

At the moment, in Europe, hydrogen is largely produced via steam reforming of methane with 60 million tons of hydrogen produced and with 500 million tons of $CO_2$. This corresponds to 2% of the world emission of $CO_2$. Moreover, there are already ten hydrogen pipelines in the world mainly in the Netherlands, Belgium and France. This hydrogen can also be transported by boat, supertanker, large cylinders and roads or by pipelines. Ethane is also a good vector for energy and the association of ethane and hydrogen is important, flexibility in the production of hydrogen and ethane is also important regarding transportation of these two gases. Although hydrogen can explode as can propane or gasoline, it has very high diffusivity in the air so that as soon as it is produced it can be diluted easily, which can improve the safety of its use. Indeed, many companies are considering the use of hydrogen either in combustion engine or better as new energy source for fuel cell (e.g., in cars). For example, for an average car trip of 500 km range, the corresponding and respective energy storage expressed in kg is the following: 33 kilos of conventional fuel; 540 kilos of lithium battery, or 6 kg (at 700 bar) of hydrogen.

Methane can be selectively coupled to form ethane or selectively decomposed to form hydrogen and a solid carbon product depending on reaction conditions, such as temperature and pressure. These two processes are commonly known as non-oxidative coupling and thermo-catalytic decomposition of methane, respectively. Surprisingly, a methane coupling catalyst can also be active in thermal decomposition of methane under different sets of operating conditions. Advantageously, ethane present with the hydrogen is easy to separate.

The context of new energy vectors in the next century shows that large scale practical solutions with low carbon dioxide foot print are really a problem. Therefore, the hydrogen generation methodology is extremely timely. Its quick development in the next 20 years will allow emerging technology to become practically feasible. Unexpectedly, methane can be catalytically coupled to ethane and hydrogen at relatively low temperature or to a higher amount of hydrogen than ethane at higher temperature.

Moreover, the formation of hydrogen and ethane does not give carbon dioxide but just carbon, which by its structure can have added value as carbon black, carbon graphite, carbon fiber, or carbon nanotube. Valorization of carbon is extremely important and can be diversified, giving the carbon product having an added value to the process of methane production.

Catalysts and reaction conditions suitable to select between the two reactions can allow for synthetic flexibility, which can lead to clean and efficient generation of hydrogen and/or solid carbon products. Importantly, the catalyst and reaction conditions can be selected to avoid rapid deactivation of the catalyst while maintaining high selectivity for hydrogen production. In certain embodiments, the structure of the solid carbon product can be controlled by selecting the temperature, pressure and catalyst used in the reaction. The solid carbon product can be carbon black, graphene, carbon microfibers, carbon nanofibers, fullerenes, carbon nanotubes (CNTs), single-walled carbon nanotubes, multi-walled carbon nanotubes, or capped carbon nanotubes.

A feed gas including methane is contacted with a metal catalyst at a selected temperature to produce a selected product. In the method, contacting methane with a metal catalyst can include adding the methane to the metal catalyst, adding the metal catalyst to the methane, or by simultaneously mixing the methane and the metal catalyst. In the method, methane can react essentially with itself to couple to form ethane, or form hydrogen and a solid carbon product depending on reaction conditions using a single metal catalyst. Advantageously, the method can produce a product including hydrogen or ethane without forming detectable amounts of carbon-containing products other than alkanes, for example of alkenes (e.g., ethylene), of alkynes (e.g. acetylene), of aromatic compounds (e.g., benzene), of carbon monoxide and/or of carbon dioxide.

The feed gas including methane can contain at least 1%, at least 10%, or at least 20% methane combined with an inert gas, such as nitrogen, helium or argon. The mole ratio of methane to catalyst can be from about 10:1 to 100,000:1, from about 50:1 to 10,000:1, or from about 100:1 to 1,000:1. The feed gas can be dry, having less than 1000 ppm, less than 100 ppm or less than 10 ppm water. The feed gas can include less than 1000 ppm water or other oxygen containing compound, such as an alcohol, carbon monoxide or carbon dioxide.

The method can be carried out at a selected temperature of about 1200° C. or less, about 1000° C., greater than about 300° C., greater than about 400° C., greater than about 500° C., greater than about 600° C., from about 600° C. to about 900° C., from about 650° C. to about 800° C. The temperature is selected to favor production of hydrogen and a solid carbon product from methane or production of ethane from methane. The ratio of hydrogen to ethane produced can vary with temperature.

The method can be carried out at a selected pressure of about 0.1 to about 100 bar, about 0.5 to about 50 bar, about 1 bar, about 5 bar, about 10 bar, about 15 bar, about 20 bar, about 25 bar, about 30 bar, about 35 bar, about 40 bar, or about 45 bar. The pressure is selected to favor production of hydrogen and a solid carbon product from methane or production of ethane from methane. The ratio of hydrogen to ethane produced can vary with pressure.

The method can be carried out as a batch or continuous process. The method can be carried out in a gas phase or a liquid phase system. For example, a fluidized bed reactor and/or a reactor with a mechanically stirred bed can be used. Alternatively, a stationary bed reactor or circulating bed reactor can be used. The gas phase of the product can be continuously removed from the reactor.

The metal catalyst can include at least one metal. In some embodiments, the metal catalyst can include two metals. The metal can be a transition metal, for example, ruthenium, nickel, iron, copper, cobalt, palladium, platinum, or combinations thereof. The catalyst can include a metal combined with a metal oxide, such as its own metal oxide. The metal can be a bimetallic or multi-metallic mixture or alloy. The catalyst can be activated by reduction with hydrogen at a temperature of between 200 and 600° C. for a number of hours. In addition to the catalysts described herein other catalysts that could be used are described, for example, in WO2011/107822, which is incorporated by reference in its entirety.

The metal can be on a solid support. The metal can be deposited on a surface of the solid support, covalently bonded to the surface of the solid support, or entrapped within the solid support. The solid support can, for example, be chosen from metal oxides, refractory oxides and molecular sieves, in particular from silicon oxides, aluminum oxides, zeolites, clays, titanium oxide, cerium oxide, magnesium oxide, niobium oxide, zinc oxide, molybdenum oxide, iron oxide, cobalt oxide, tantalum oxide or zirconium oxide. The metal catalyst can include a metal hydride.

The metal of the metal catalyst, or the support, or both, can have nanoscale features. For example, the metal can be in the form of metal nanoparticles having average diameters of less than 200 nm, for example, 5 nm, 10 nm, 15 nm, 20 nm, 30 nm, 40 nm, or 50 nm. The nanoparticles can be spherical or aspherical. The support can have nanoscale features of less than 200 nm, for example, 5 nm, 10 nm, 15 nm, 20 nm, 30 nm, 40 nm, or 50 nm. The nanoparticles can be spherical or aspherical. The support can be, for example, a silica nanoparticle. Suitable nanoparticles can be prepared as described in V. Polshettiwar, et al., Angew. Chem. Int. Ed. 2010, 49, 9652-9656, which is incorporated by reference in its entirety.

Methane decomposition is an endothermic process. Introduction of high temperature condition in the reactor system improves the carbon accumulation and increases the methane conversion by switching the equilibrium to the right. Nevertheless, high temperature condition is subjected to faster deactivation of catalyst. To keep the stability of the catalyst, lower reaction temperature is applied or with diluted methane, but these reduce the catalytic activity.

Reaction temperature can have a great influence on catalyst activity, catalyst lifetime and morphology of the solid carbon product that is produced. Temperature elevation can result in a disproportionately rapid catalyst deactivation. At high temperature, the catalyst can be in a quasi-liquid state where the catalyst particles are easily cut into small particles and the small particles that can be easily encapsulated by the carbon layer formed during methane decomposition, contributing to faster catalyst deactivation. At low temperature, the catalyst remains in solid state rather than in quasi-liquid state and it sustains the activity of catalysis process. Selection of the proper catalyst material can result in catalyst surfaces that do not foul from carbon deposition during the process. In certain examples, ruthenium catalysts are particularly suitable to avoid fouling from carbon deposition.

Carbon nanotube production can be preferable at moderate temperature in order to prolong the catalyst lifetime, but can result in low methane conversion. Low methane conversion can be addressed by separation of the methane-hydrogen mixture at the reactor effluent, followed by recycling of methane. Alternatively, a membrane reactor can be used to remove continuously produced hydrogen from methane decomposition reaction. This alternative can increase methane conversion and enhance the lower temperature reaction. Separation of methane from hydrogen product can increase the operation cost and the hydrogen permeating membrane makes the reactor structure complex. This catalyst system and the optimum operating conditions are expected to contribute effectively towards large-scale production of carbon nanotubes and hydrogen through methane decomposition reaction by using methane gas as carbon source.

Figure 11:
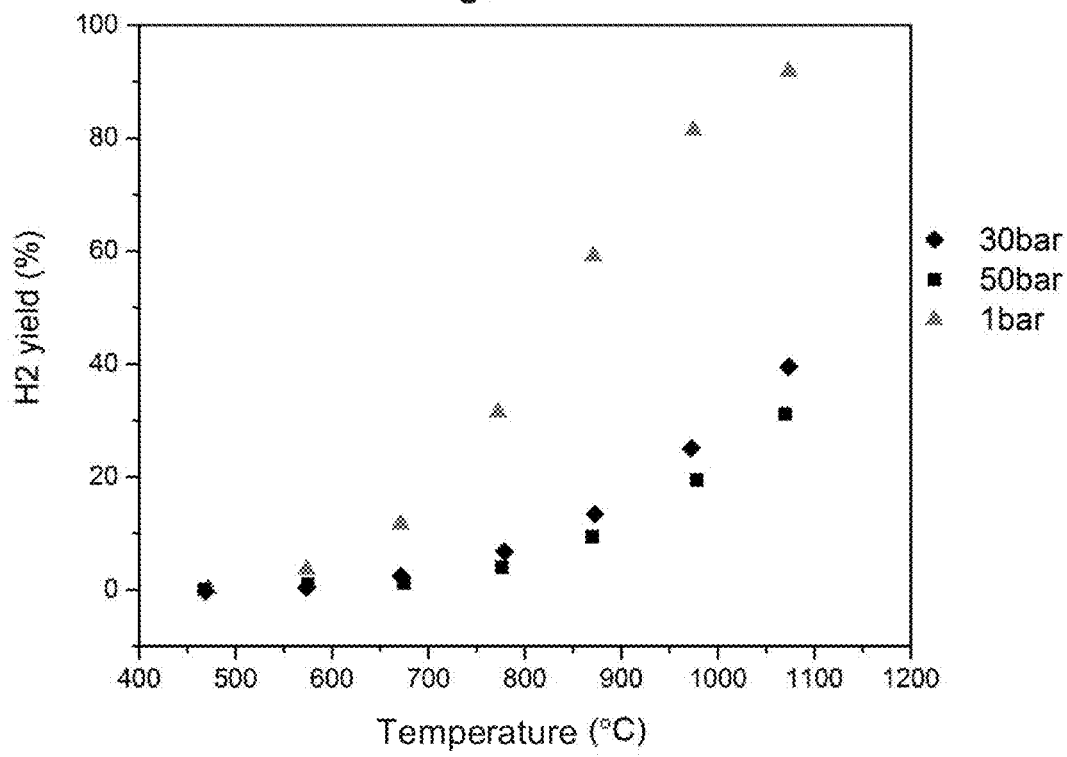
FIG. 11 is a graph depicting thermodynamic minimization of Gibbs free energy assuming a system with the following components; $CH_4$ (gas), $C_2H_6$ (gas), $H_2$ (gas), and C (graphite) at 1 bar, 30 bar and 50 bar.

Thermodynamics calculations based on the minimization of Gibbs free energy assuming a system with the following components; $CH_4$ (gas), $C_2H_6$ (gas), $H_2$ (gas), and C (graphite) was carried out at various pressures. The results of the thermodynamics calculation at 1 bar, 30 bar and 50 bar are shown in FIG. 11.

B.

In addition, embodiments of the present disclosure also provide for a supported fused Fe catalyst, a method of making the supported fused Fe catalyst, methods of hydrocarbon decomposition, and the like. Embodiments of the supported fused Fe catalyst can be used for the industrialization of MCD processes. In particular, the supported fused Fe catalyst is highly active, has a long useful lifetime, selective, and is stable, unlike other catalysts in MCD processes. In addition, the supported fused Fe catalyst can be used in the Fischer Tropsch process, to synthesize ammonia as well as in DRM, SRM, POM or their combinations. In particular, the supported fused Fe catalyst is more efficient than the typical catalyst used in the preparation methods in DRM.

The deactivation of catalysts by the carbon deposition during the MCD is one of main issues that hinder the practical utilization of MCD. The present disclosure provides a supported fused Fe catalyst that is highly stable in the process of MCD. The present disclosure also provides an alternative way to activate the catalyst using a reactant gas (e.g., methane) instead of $H_2$. This kind of in-situ activation method may result advantageous catalyst performance during the process of MCD.

Embodiments of the present disclosure provide for supported fused Fe catalysts. In a particular embodiment, the supported fused Fe catalyst is a fused $Fe/Al_2O_3$ catalyst, which is distinctive from impregnated $Fe/Al_2O_3$, as described in more detail below and in the Example. In an embodiment, the Fe content in the supported fused Fe catalyst can be about 5 to 65 wt % of the supported fused Fe catalyst. In an embodiment, the alumina support can be replaced with one or more of the following: silica, silica-alumina, zirconia, titania, zinc oxide, magnesia, zeolite, mesoporous zeolite, and the like, and a combination thereof. In an embodiment, the supported fused Fe catalyst $Fe/Al_2O_3$ has a spinel structure; catalysts with spinel structure are rarely used in the MCD reaction.

Figure 3:
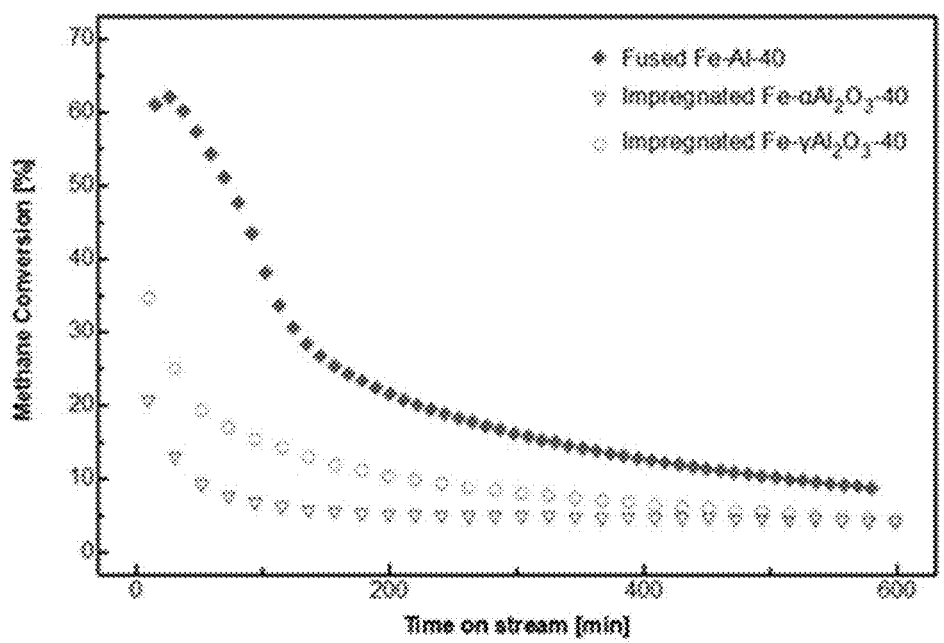
FIG. 3 is a graph illustrating a comparison of activity between fused and impregnated Fe—$Al_2O_3$ catalysts. Reaction condition: 750° C., SV 7.5 $L/h·g_{cat}$.

As described in more detail in the Example, the XRD profile of the supported fused Fe catalyst does not include a peak for $Al_2O_3$ as opposed to impregnated $Fe/Al_2O_3$ catalyst includes a peak for $Al_2O_3$. In addition, the supported fused Fe catalyst has greater activity than impregnated $Fe/Al_2O_3$ catalyst as shown in FIG. 3. The fused catalyst shows an initial methane conversion of 60%, whilst the impregnated catalysts showed a much lower methane conversion between 20-35%.

In an embodiment, the supported fused Fe catalyst can be red mud or red sludge, which is a waste product generated in the industrial production of aluminum during Hall-Héroult process. Red mud is composed of a mixture of solid and metallic oxides. The red color arises from iron oxides, which comprise up to about 60% (e.g., about 5 to 60%, about 15 to 60%, about 25 to 60%, about 40 to 60%) of the mass of the red mud. Although not intending to be bound by theory, the Hall-Héroult process provides a similar environment similar to that of the fusion method described herein. In an embodiment, when red mud is used as the supported fused Fe catalyst it shows good MCD activity (See FIG. 11 in the Example).

The present disclosure also discloses a method that is used to prepare supported catalysts with strong metal-support interaction, especially designed to help the formation of a spinel structure. In an embodiment, the method of making the supported fused Fe catalyst includes physically grinding and mixing a Fe nitrate and a support nitrate. In an embodiment, the components can be grinded using a grinder and/or kneader device. In an embodiment the component can be ground until both the nitrate precursors are homogeneously mixed. The mixture can then be calcined under static air from about room temperature to 300-1100° C. for about 2 to 4 h or about 3 h with a 3 to 8° C./min latter or 5° C./min latter. The mixture can be calcined in a muffler. After calcination, the temperature can be reduced to room temperature under air flow to form the supported fused Fe catalyst. The product can be grinded into a fine powder of 200-400 μm to form the final product of the supported fused Fe catalyst.

In an embodiment, the support nitrate can be aluminum nitrate, magnesium nitrate, calcium nitrate, or a combination thereof. The amount of the support nitrate and the Fe nitrate can be adjusted to produce a supported fused Fe catalyst that has a Fe content of about 5 to 65 wt % of the supported fused Fe catalyst.

The present disclosure also discloses a process for the decomposition of hydrocarbons (e.g., MCD) using the catalyst disclosed herein. In addition, the present disclosure further discloses a method for the activation of the catalyst using $H_2$ or the hydrocarbon.

In an embodiment, hydrocarbon catalytic decomposition to form $H_2$ can be accomplished by heating the supported fused Fe catalyst to about 400-1000° C. under an inert gas (e.g., Ar). Subsequently, a hydrocarbon (e.g., methane) can be flowed across the supported fused Fe catalyst. A catalytic reaction causes the decomposition of the hydrocarbon to produce $H_2$. In a particular embodiment, the flowing the hydrocarbon across the supported fused Fe catalyst reduces (activates) the supported fused Fe catalyst to Fe, which can react with the hydrocarbon to produce $H_2$. In another embodiment, the supported fused Fe catalyst can be pre-activated using $H_2$. Specifically, prior to introduction of the hydrocarbon to the catalyst, the supported fused Fe catalyst is heated to the reduction temperature of the supported fused Fe catalyst at 400-1000° C. and then $H_2$ is flowed over the supported fused Fe catalyst to reduce the supported fused Fe catalyst. Additional details regarding the decomposition of the hydrocarbon are provided in the Example.

In an embodiment, the hydrocarbon can include saturated and unsaturated hydrocarbons such as C1-C20 alkanes, C2-C20 alkenes, C2-C20 alkynes, and a mixture thereof, where each can be linear, branched, cyclic, aromatic, or a mixture thereof. In an embodiment, the hydrocarbon can be methane.

In an embodiment, the hydrocarbon mixture can be just the natural gas coming from the ground with simple dehydration and desulfuration steps.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

The present disclosure provides a series of supported Fe catalyst with the Fe loading in the range of 5 to 65 wt. % (catalysts A to G, see Table 1). The present disclosure also discloses a method that is used to prepare supported catalysts with strong metal-support interaction, especially designed to help the formation of a spinel structure; a process for the MCD using the catalyst; a method for the activation of the catalyst, and that the Fe is the active phase for the MCD, while the fused $FeAl_2O_4$ is a better precursor to provide stable Fe that other Fe-oxides.

Materials and General Consideration:

Unless otherwise stated, all reagents were purchased from commercial suppliers and used as received. Iron nitrate nonahydrate (98%) and Aluminum Nitrate nonahydrate (99.997%) were purchased from Sigma-Aldrich and used as received. $Fe/Al_2O_3$ materials (Table 1) were prepared according to the procedure named as fusion method; a typical procedure is described as follows:

Physically grinding and mixing Fe nitrate and support nitrate

Calcining under static air from R.T. to 350° C. for 3 h with a 5° C./min

Going down to RT under air flow, and then grinding the final sample to fine powder The range of Fe loading can be from about 5-65 wt. %, as determined by elemental analysis.

Elemental analyses were obtained from the service of Mikroanalytisches Labor Pascher (Remagen, Germany). XRD patterns were recorded on a Bruker D8 Advanced A25 diffractometer using a Bragg-Brentano geometry with a copper tube operating at 40 kV and 40 mA. The catalyst powder was compacted into disks and mounted in the chamber. The mean crystallite sizes of Fe and Fe-oxides were calculated using the Scherrer equation. $N_2$ adsorption-desorption isotherms were obtained on a Micromeritics ASAP2420. Prior to these measurements, the samples were degassed for 2 h at 300° C. The surface areas of the samples were determined by a multi-point BET analysis method, and pore volumes were estimated at $P/P_0=0.99$. $H_2$-TPR was performed on an Altamira instrument. The catalyst powder (50 mg) was placed in a U-shaped quartz reactor and pre-treated in flowing Ar (50 mL/min) for 0.5 h at 300° C., followed by cooling to room temperature. The temperature was then raised from room temperature to 1000° C. at a rate of 10° C./min under a 5% $H_2$/Ar flow (50 mL/min). A thermal conductivity detector (TCD) was employed to monitor the $H_2$ consumption. Similarly, the $O_2$-TPO was monitored with the same instrument by using the 5% $O_2$/He instead of $H_2$/Ar flow. Scanning electron microscope (SEM) images were taken by the FEI Quanta 200 or 600 FEG environmental scanning electron microscope (ESEM). TEM images were taken on a Titan G2 transmission electron microscope (FEI, Hillsboro, Oreg., USA), operating at 80-300 kV and equipped with a 4 k×4 k charge-coupled device (CCD) camera (US4000) and energy filter (GIF Tridiem, Gatan Inc., Pleasanton, Calif., USA). The specimens were prepared by ultrasonically suspending the sample in ethanol. A drop of the suspension was then applied onto clean holy copper grids and dried in air.

TABLE 1

Example 1 Properties of catalysts A to G

| Catalysts | Fe loading [wt %] | BET [m2/g] | Pore volume [cc/g] | Pore size [nm] |
|---|---|---|---|---|
| A | 5 | 145 | 0.15 | 3.68 |
| B | 10 | 162 | 0.16 | 3.47 |
| C | 20 | 203 | 0.24 | 4.07 |
| D | 35 | 184 | 0.23 | 4.00 |
| E | 40 | 174 | 0.26 | 4.83 |
| F | 50 | 116 | 0.19 | 5.07 |
| G | 65 | 57 | 0.20 | 11.77 |

FIG. 1 shows the XRD profiles over the prepared $Fe/Al_2O_3$ catalysts in this project. The fusion method must be an excellent way to enhance the interaction between support and metal, because no peak was detected for the $Al_2O_3$, whereas the peak that belonged to the hercynite $FeAl_2O_4$ can be strongly detected. As a comparison experiment, a $Fe/Al_2O_3$ catalyst with 35 wt. % Fe loading assigned as H was prepared by wet incipient impregnation method as follows Measure water absorption percentage of γ-$Al_2O_3$ supports, γ-$Al_2O_3$ (Aeroxide® Alu C, fumed aluminium oxides, specific surface area 130±15 m²/g) was purchased from Evonik Industries. Prior to use, γ-Al$_2$O$_3$ was aggregated by treatment with distilled water and dried in the oven at 120° C. for 2 days. The void volume of γ-Al$_2$O$_3$ is 0.5 ml/g, determined by water impregnation.

Figure 2:
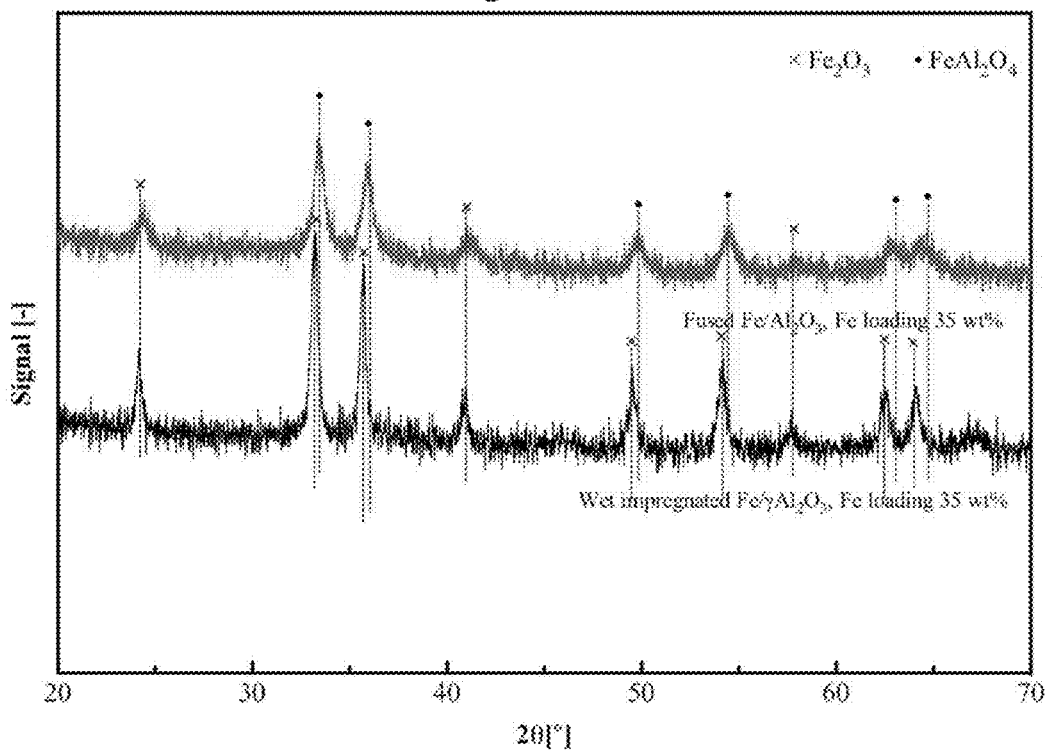
FIG. 2 illustrates a comparison of XRD results over prepared fresh $Fe/Al_2O_3$ catalysts with different methods.
Figure 4:
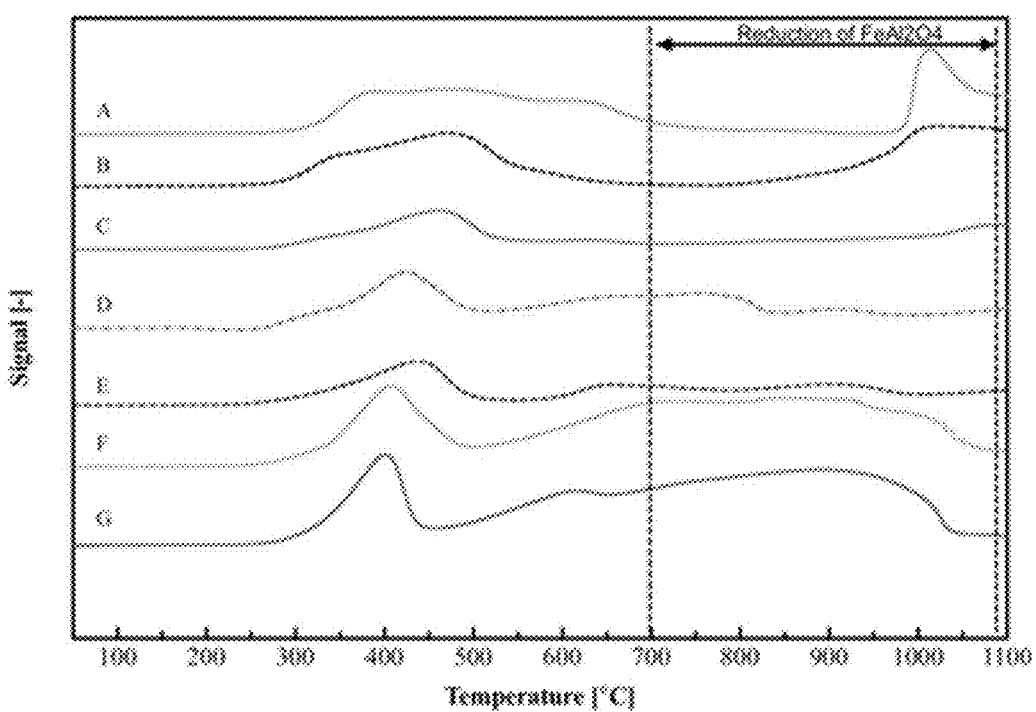
FIG. 4 is a graph that illustrates $H_2$-TPR profiles over fused $Fe/Al_2O_3$ samples.
Figure 5:
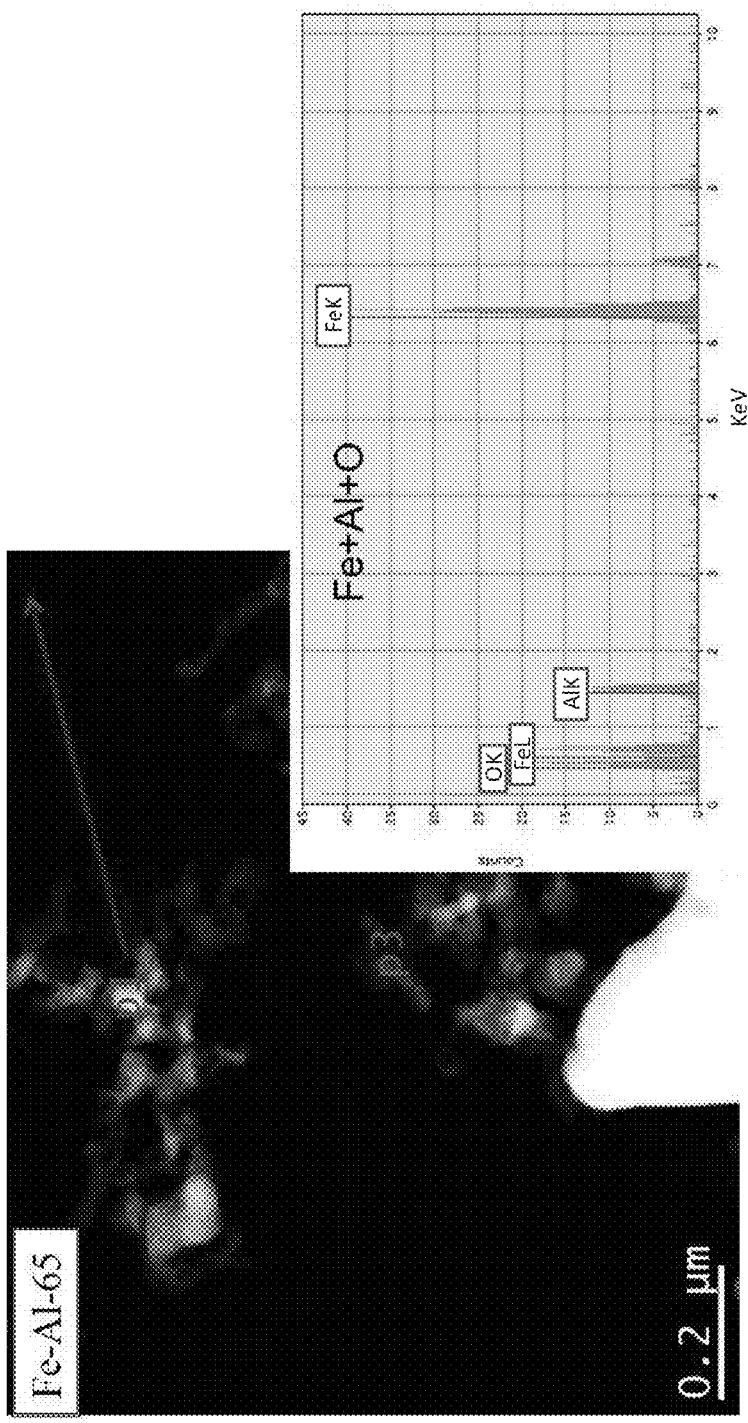
FIG. 5 illustrates STEM and EDX analyses over $Fe/Al_2O_3$ with 65 wt. % Fe loading.
Figure 6D:
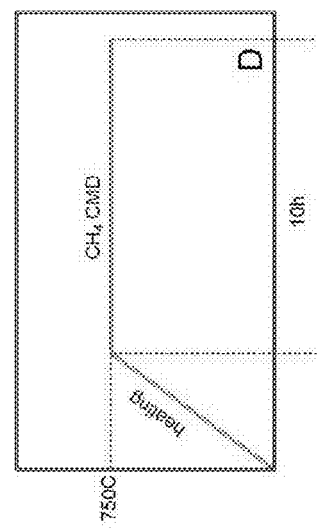
FIGS. 6A to 6D illustrate graphs of different reaction modes: [6A] 900° C. $H_2$-reduction; [6B] 750° C. $H_2$-reduction; [6C] 500° C. $H_2$-reduction; [6D] 750° C. $CH_4$-reduction.
Figure 6A:
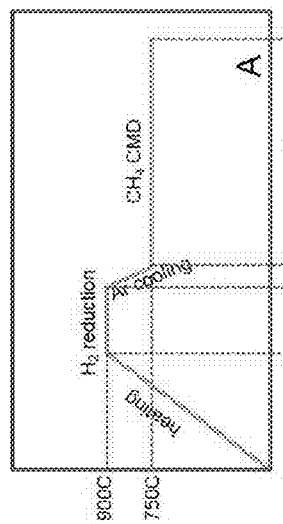
Figure 6B:
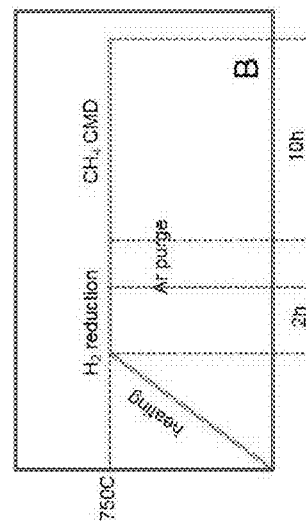
Figure 6C:
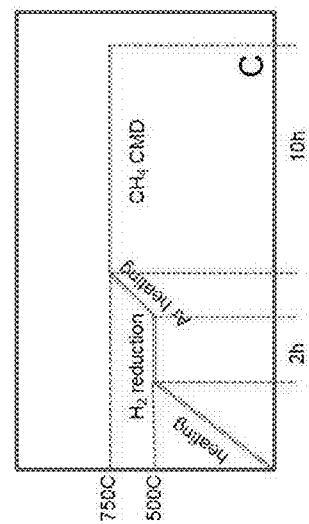

Incipient impregnation with Fe nitrate water solution
Dry 110° C. for over night
Calcination at 450° C. for 8 h with a 5° C./min ramp
Grind to homogeneous particles FIG. 2 compares the XRD patterns over fused and impregnated Fe/Al$_2$O$_3$ catalysts with 35 wt. % Fe loading. It is clear that the fused catalyst has a stronger metal-support interaction than that of impregnated catalyst, since no FeAl$_2$O$_4$ can be found on latter catalyst. It is likely that during the fusion process the mixed salts of Fe and Al nitrate would undergo thermal decomposition then a phenomenon of partial fusion (the percentage of how much salts are melted is reasonable to be related to the fusion temperature). The different Fe and Al interaction mechanism between the fused and impregnated catalysts may be a possible explanation for the different metal-support interaction. The existence of FeAl$_2$O$_4$ over fused Fe/Al$_2$O$_3$ catalysts was further evidence by H$_2$-TPR profiles in FIG. 4. The reduction of Fe-oxide (Fe$_2$O$_3$ and Fe$_3$O$_4$) usually finish at low temperature zone—700° C. Therefore the reduction peaks shown at high temperature zone between 700-1100° C. must be assigned to the FeAl$_2$O$_4$ reduction. The EDX analyses over fused Fe/Al$_2$O$_3$ in FIG. 5 further demonstrated the FeAl$_2$O$_4$ existence.

A typical MCD test is described as follows: The catalytic reaction was conducted in a PID micro reactor equipped with a long quartz tube reactor (ID 14 mm, length 305 mm), which was heated by an electrical furnace under atmosphere pressure. The catalyst was loaded into the reactor, while the reaction temperature was controlled by a thermocouple placed into the middle of the catalyst layer. The CH4 used for the MCD was not diluted, while the total gas flow rate was fixed at the same value of 10 mL/min. The catalysts amount was varied among 40-240 mg in order to get a different GHSV of 1.875-15 L/h·gcat. As shown in FIG. 6, two reaction modes were adopted here. For mode 1, after loading the catalyst, the reactor was heated to reduction temperature with Ar, and then the flowing gas was switched to H$_2$ to reduce the catalyst at selected temperature for 2 h. After this pre-reduction treatment, the gas was switched back to Ar to heat or cool or purge the catalyst to 750° C. After this, the gas was again changed to 10 mL/min reacting CH$_4$ to start the MCD reaction for 10 h. For mode 2, the loaded catalyst was directly heated to 750° C. under Ar, in the absence of hydrogen and then the gas was switched to 10 mL/min CH$_4$ to begin the MCD reaction. The outlet gases were analyzed by an online GC (Varian 450-GC) and micro GC (Soprane MicroGC 3000).

Figure 7:
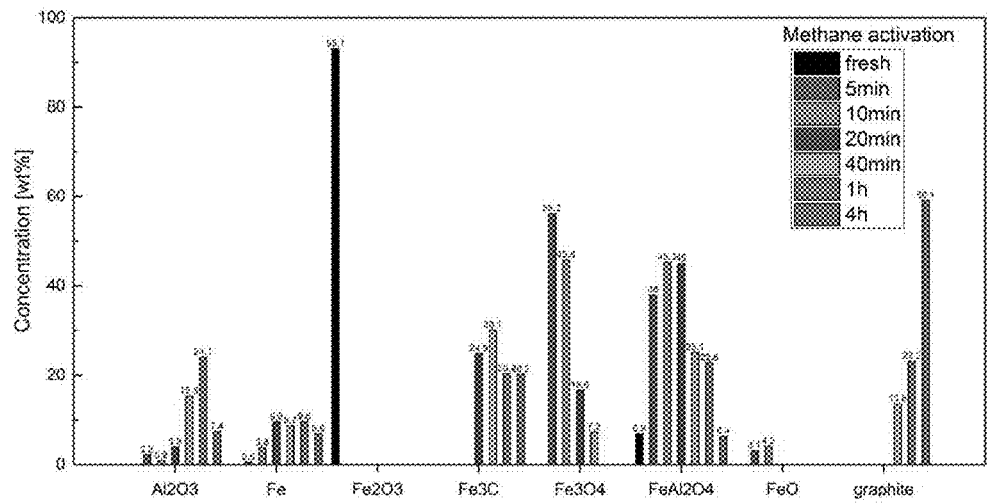
FIG. 7 is a graph that illustrates Fe—Al-40 catalyst composition change during 750° C. $CH_4$-reduction with time on stream.

For the mode 2 where the catalysts are activated by methane gas, a semi insitu XRD analyses over the catalysts composition change during this treatment was conducted in FIG. 7. It is obviously that using methane to activate the catalyst helps to form more FeAl$_2$O$_4$ species. And the Fe later reduced from this FeAl$_2$O$_4$ is believed to show better reactivity than that from normal Fe-oxides. The Fe is the active phase for the MCD reaction, while the FeAl$_2$O$_4$ is the best precursor to provide stable Fe for this MCD.

Figure 8:
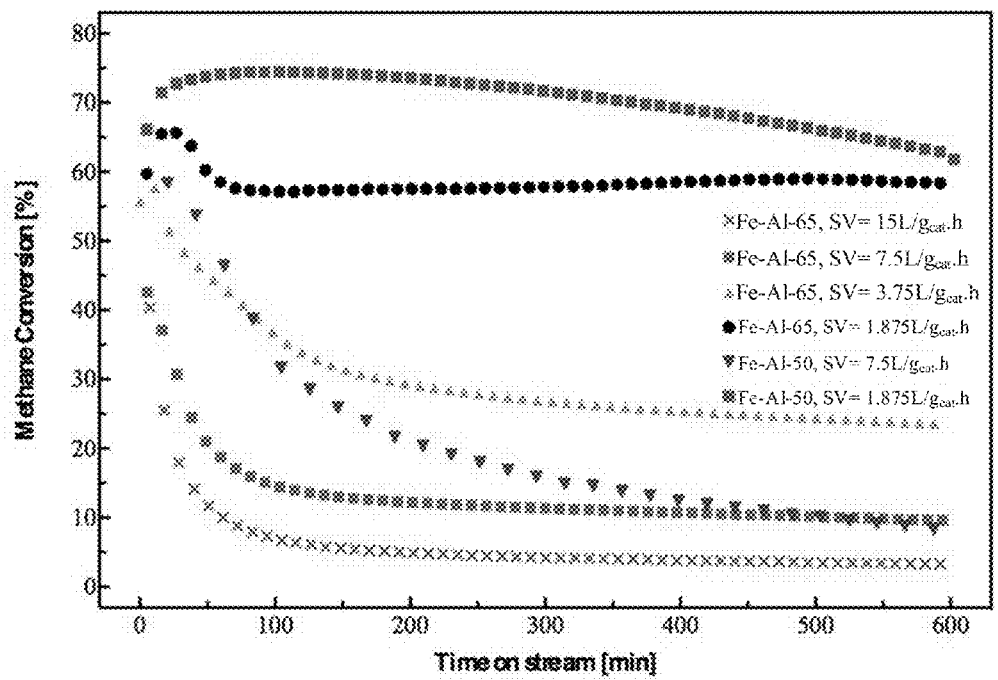
FIG. 8 is a graph that illustrates the influence of GHSV over catalysts MCD performance.
Figure 9:
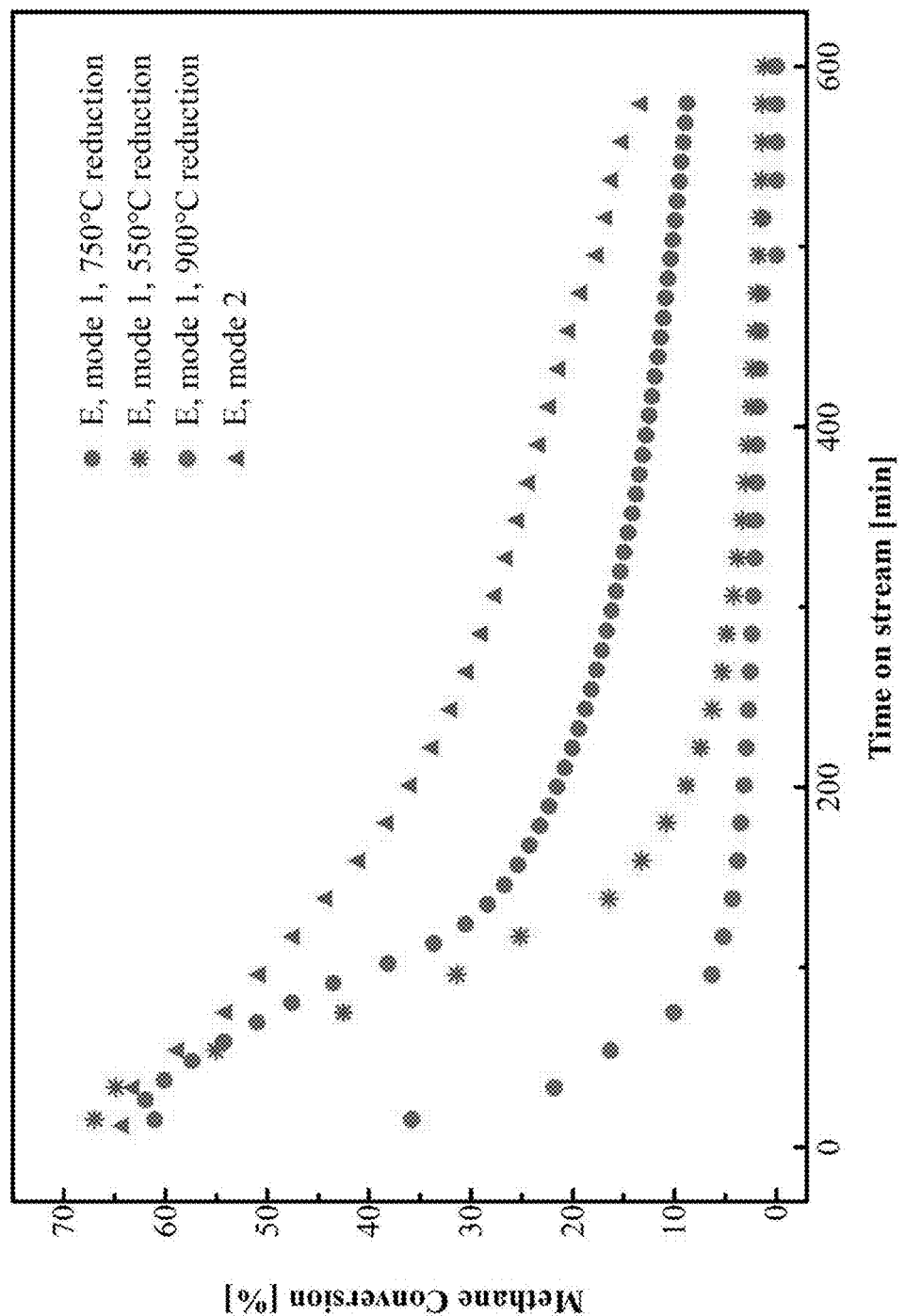
FIG. 9 is a graph that illustrates the influence of pretreatment over catalysts MCD performances.
Figure 10:
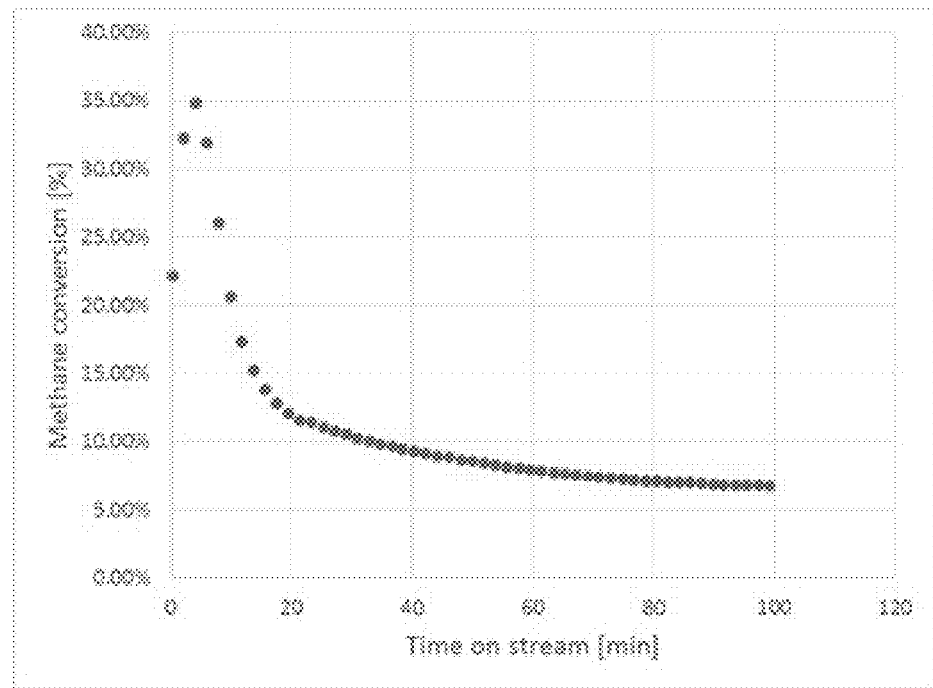
FIG. 10 is a graph that illustrates CMD over red mud. Reaction condition: 900° C., SV 7.5 $L/h·g_{cat}$.

The reaction results are summarized in Table 2, Example 1 and FIGS. 8 and 9.

TABLE 2

Example 1 Summarization of the MCD results over catalysts

| Catalysts | Reaction temp. [° C.] | Reaction GHSV [L/h · g$_{cat}$] | Activation mode | Initial CH4 conversion [%] | Carbon deposited amount [g-C/g-Fe] | H2 production [mol H2/g-Fe] |
|---|---|---|---|---|---|---|
| A | 750 | 7.5 | Mode 1, H$_2$ 750° C. | 1.2 | 2.6 | 0.43 |
| B | 750 | 7.5 | Mode 1, H$_2$ 750° C. | 2.5 | 4.6 | 0.77 |
| C | 750 | 7.5 | Mode 1, H$_2$ 750° C. | 13.8 | 7.9 | 1.32 |
| D | 750 | 7.5 | Mode 1, H$_2$ 750° C. | 51.2 | 20.3 | 3.38 |
| E | 750 | 7.5 | Mode 1, H$_2$ 750° C. | 62.0 | 20.8 | 3.47 |
| E | 750 | 7.5 | Mode 1, H$_2$ 550° C. | 66.9 | 12.3 | 2.05 |
| E | 750 | 7.5 | Mode 1, H$_2$ 900° C. | 35.8 | 4.1 | 0.68 |
| E | 750 | 7.5 | Mode 2 | 64.4 | 31.0 | 5.17 |
| F | 750 | 7.5 | Mode 1, H$_2$ 750° C. | 58.4 | 15.3 | 2.55 |
| F | 750 | 1.875 | Mode 1, H$_2$ ° C. | 74.5 | 18.8 | 3.13 |
| G | 750 | 15 | Mode 1, H$_2$ 750° C. | 40.4 | 7.1 | 1.18 |
| G | 750 | 7.5 | Mode 1, H$_2$ 750° C. | 42.6 | 8.0 | 1.33 |
| G | 750 | 3.75 | Mode 1, H$_2$ 750° C. | 57.7 | 9.2 | 1.53 |
| G | 750 | 1.875 | Mode 1, H$_2$ 750° C. | 65.6 | 11.8 | 1.97 |
| H | 750 | 7.5 | Mode 1, H$_2$ 750° C. | 35.2 | 9.4 | 1.57 |

Example 2

Catalyst Preparation
Preparation of KCC-1-NH$_2$:
To a 25 mL round-bottom flask, 150 mL of anhydrous toluene, 12.00 g KCC-1, and 40 mL of 3-aminopropyltriethoxysilane (APTS) were successively introduced. The mixture was refluxed for 48 h. The solution was filtered, the solid was washed with acetone and chloroform, and the solid was dried overnight at 65 degree C. under vacuum to yield the KCC-1-NH$_2$ nano-composite. Synthesis of suitable catalysts are described, for example, in WO2011/107822, which is incorporated by reference in its entirety.

Preparation of Catalysts (KCC-1-NH$_2$/Ru NPs, KCC-1-NH$_2$/Fe NPs, KCC-1-NH$_2$/Co NPs):
A Schlenk flask was charged with 3 g of KCC-1-NH$_2$ material and the required amount of metal chloride (e.g., RuCl$_3$, FeCl$_2$, CoCl$_2$), (e.g., 0.21 g of RuCl$_3$) was sonicated in 50 ml of deionized water for 2 h. The mixture was stirred for 72 h at room temperature. The solid was collected by centrifugation and washed several times with water, ethanol and acetone. The solid was then dried under reduced pressure at 65 degree C. for 16 h, which resulted in a grey powder (3.2 g). The reduction was performed in a fixed-bed continuous flow reactor. For the in situ preparation of the ruthenium nanoparticles, the unreduced catalyst (200 mg) was placed in a stainless steel tubular reactor with a 9-mm internal diameter and was reduced in a stream of hydrogen (20 mL/min) at 400 degree C. for 16 h. The ruthenium content of the final material was determined by ICP elemental analysis and was found to be 4.2%.

Catalytic Tests. The catalytic tests for methane coupling and/or decomposition were carried out in a fixed-bed continuous flow reactor. The powdered catalyst was charged in a stainless steel tubular reactor that was placed in an electric furnace. The temperature in the reactor was controlled by a PID temperature controller connected to the thermocouple placed inside catalyst bed and maintained with a frit.

The catalytic activity was determined by filing the reactor with $N_2$ until reaching 30 bar. Methane was allowed to pass over the catalyst at a rate varied between 3 and 12 mL/min. The individual gas flow rates were controlled using mass flow controllers, previously calibrated for each specific gas. The activity of the catalyst was tested continuously several hours, by keeping the catalyst at a constant temperature, until the conversion is stabilized.

The feed gases and the products were analyzed employing an online Gas Chromatograph equipped with TCD and FID detectors using He and $H_2$ as a carrier gases respectively.

First of all, the idea was to test catalysts in the reaction of methane coupling (equation 1) and to study the effect of the temperature under isobar conditions (30 bars).

By definition, the conversion of methane is $$\text{conversion} = \frac{n(CH4)in - n(CH4)out}{n(CH4)in}$$

Assuming the following two reactions:

$$2CH_4 \rightarrow C_2H_6 + H_2$$

$$CH_4 \rightarrow C_{(3)} + 2H_2$$

From carbon balance, The number of moles of methane introduced should be equal to n(CH4)in=n(CH4)+2n(C2H6)+n(c).

However, n(c) is unknown, but can be estimated as follows:

The total number of moles of $H_2$ in the gas phase is $n(H_2) = n(H_2)$ coupling $+ n(H_2)MD =$ methane decomposition $n(H_2)$ coupling $= n(HC_2H_6)$ $$\text{conversion} = \frac{1.5n(C_2H_6) + 0.5n(H_2)}{n(CH_4) + 1.5n(C_2H_6) + 0.5n(H2)}$$

Assuming that there is no significant change in total number of moles before and after reaction;

$$\text{conversion} = \frac{1.5x(C_2H_6) + 0.5x(H_2)}{x(CH_4) + 1.5x(C_2H_6) + 0.5x(H2)};$$

x=molar fraction determined from GC

Yield of $H_2$: Each mole of $CH_4$ gives ideally a maximum of 2 moles of $H_2$.

Thus, $$H2 \text{ yield } (\%) = \frac{n(H2)}{2n(CH_4)in}$$

$$H2 \text{ yield } (\%) = \frac{n(H2)}{2 \times (n(CH_4) + 1.5n(C_2H_6) + 0.5n(H2))}$$

Yield of C2: Each mole of CH.4 gives ideally a maximum of 0.5 moles of $C_2H_6$, Thus, $$C2 \text{ yield } (\%) = \frac{n(C_2H6)}{0.5n(CH_4)in}$$

$$C2 \text{ yield } (\%) = \frac{n(C_2H6)}{0.5 \times (n(CH_4) + 1.5n(C_2H_6) + 0.5n(H2))}$$

Catalyst Runs

Reactions were carried out using as a catalyst KCC-1/Ru nanoparticles, 4.1 wt % Ru. Unless otherwise noted, the reactions used 200 mg catalyst, pressure 29 bar, methane flow of 3 ml/min.

The data in Table 1, Example 2 (below) were for reactions carried out regeneration of catalyst (15 h at 400° C. under an $H_2$ flow of 20 ml/min).

TABLE 1

| Conditions | | | Experimental | | | | Thermodynamics | | | |
|---|---|---|---|---|---|---|---|---|---|---|
| Catalyst loading (mg) | Temperature (° C.) | $CH_4$ (ml/min) | Molar Ratio ($H_2$/C2) | Conversion (%) | $C_2$ Yield (%) | $H_2$ Yield (%) | Conversion (%) | H2/C2 | H2 yield | C2 Yield (%) |
| 200 | 400 | 3 | 5.65 | 0.32 | 0.16 | 0.2 | 2.3 | 316 | 2.3 | 0.01 |
| 200 | 400 | 3 | 5.33 | 0.31 | 0.14 | 0.2 | 2.3 | 316 | 2.3 | 0.01 |
| 200 | 500 | 3 | 45.59 | 1.14 | 0.1 | 1.07 | 6.1 | 557 | 6.1 | 0.02 |
| 200 | 500 | 3 | 5.58 | 0.28 | 0.13 | 0.18 | 2.3 | 316 | 2.3 | 0.01 |
| 200 | 400 | 6 | 3.66 | 0.22 | 0.13 | 0.12 | 2.3 | 316 | 2.3 | 0.01 |
| 200 | 400 | 9 | 5.36 | 0.22 | 0.11 | 0.13 | 2.3 | 316 | 2.3 | 0.01 |
| 200 | 400 | 12 | 7.31 | 0.08 | 0.01 | 0.07 | 2.3 | 316 | 2.3 | 0.01 |
| 500 | 400 | 6 | 3.72 | 0.24 | 0.14 | 0.13 | 2.3 | 316 | 2.3 | 0.01 |
| 500 | 400 | 6 | 3.13 | — | — | — | 2.3 | 316 | 2.3 | 0.01 |
| 500 | 600 | 3 | 290.09 | 5.08 | 0.07 | 5.03 | 13.3 | 1987 | 13.3 | 0.03 |
| 500 | 700 | 3 | 857.05 | 12.7 | 0.06 | 12.6 | 24.5 | 3090 | 24.5 | 0.03 |

-continued $n(H_2)MD = 2n(C)$ $$n(c) = \frac{n(H_2) - n(C_2H6)}{2}$$

It is notable that the experimental yields of $C_2$ are higher than those expected from thermodynamics.

Additional experiments using iron or cobalt metals as catalysts were conducted, and the results are summarized in Table 2, Example 2 (below).

TABLE 2

| catalyst | Temp (° C.) | Time (h) | CH$_4$ (ml/min) | H$_2$/C$_2$H$_6$ molar ratio | Conversion (%) | C$_2$H$_6$ yield (%) | H$_2$ yield (%) | C yield (%) |
|---|---|---|---|---|---|---|---|---|
| KCC-1/Fe NPs | 600 | 24 | 3 | n/a | 3.23 | Not measured | 2.16 | 1.08 |
| | 700 | 24 | 3 | n/a | 23.70 | Not measured | 15.80 | 7.90 |
| | 800 | 24 | 3 | n/a | 99.34 | Not measured | 66.23 | 33.11 |
| KCC-1/Co NPs | 600 | 24 | 3 | n/a | 0.68 | Not measured | 0.45 | 0.23 |
| | 700 | 24 | 3 | n/a | 8.48 | Not measured | 5.65 | 2.83 |
| | 800 | 24 | 3 | n/a | 99.77 | Not measured | 66.52 | 33.26 |

The obtained results indicated two parallel competitive reactions can take place: i) coupling of methane into ethane, and ii) thermal decomposition of methane to hydrogen and carbon.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A method of selectively producing hydrogen or ethane from methane, comprising:
    selecting a first temperature to produce a first selected product, wherein the first temperature is selected to favor either a predominately (a) hydrogen and solid carbon product or (b) ethane and hydrogen product;
    contacting a feed gas containing methane, with a single catalyst at the first temperature to produce the first selected product, wherein the single catalyst is a supported fused FeAl$_2$O$_4$ catalyst;
    selecting a second temperature to produce a second selected product, wherein the second selected product is different from the first selected product; and
    contacting a feed gas containing methane, with the single catalyst at the second temperature to produce the second selected product.

2. The method of claim 1, wherein Fe is about 5 to 65 wt. % of the single catalyst.

3. The method of claim 1, wherein the support includes one or more of silicon oxide, aluminum oxide, titanium oxide, zirconium oxide, magnesium oxide, cerium oxide, zinc oxide, molybdenum oxide, iron oxide, nickel oxide, cobalt oxide, and graphite.

4. The method of claim 1, wherein the fused catalyst includes red mud generated from industrial production of aluminum.

* * * * *